(12) United States Patent
Wehner et al.

(10) Patent No.: US 10,448,859 B2
(45) Date of Patent: Oct. 22, 2019

(54) MOUNTING ASSEMBLY FOR A MAGNETIC FIELD GENERATOR

(71) Applicant: St. Jude Medical, Cardiology Division, Inc., St. Paul, MN (US)

(72) Inventors: Peter Wehner, Brooklyn Park, MN (US); Lawrence Swanson, White Bear Lake, MN (US); Adam Fischbach, Inner Grove Heights, MN (US)

(73) Assignee: St. Jude Medical, Cardiology Division, Inc., St. Paul, MN (US)

( * ) Notice: Subject to any disclaimer, the term of this patent is extended or adjusted under 35 U.S.C. 154(b) by 465 days.

(21) Appl. No.: 15/401,158

(22) Filed: Jan. 9, 2017

(65) Prior Publication Data
US 2017/0196477 A1    Jul. 13, 2017

Related U.S. Application Data

(60) Provisional application No. 62/278,215, filed on Jan. 13, 2016.

(51) Int. Cl.
*A61G 13/10* (2006.01)
*A61B 5/06* (2006.01)
(Continued)

(52) U.S. Cl.
CPC ............... *A61B 5/062* (2013.01); *A61B 5/05* (2013.01); *A61B 5/704* (2013.01); *A61G 13/101* (2013.01); *A61G 13/128* (2013.01); *A61M 25/0127* (2013.01); *A61B 2034/2051* (2016.02); *A61B 2034/733* (2016.02); *A61B 2562/0223* (2013.01); *A61B 2562/12* (2013.01)

(58) Field of Classification Search
CPC ... A61B 50/15; A61G 13/101; A61G 13/0018
See application file for complete search history.

(56) References Cited

U.S. PATENT DOCUMENTS 2,588,124 A * 3/1952 Kizaur ................... A61B 6/00
378/177
2,854,676 A   10/1958 Fried et al.
(Continued)

FOREIGN PATENT DOCUMENTS

GB            1600136 A    10/1981

*Primary Examiner* — Kennedy Schaetzle
(74) *Attorney, Agent, or Firm* — Armstrong Teasdale LLP

(57) ABSTRACT

The present disclosure provides a mounting assembly for attaching medical equipment to a patient table. In one particular embodiment, the present disclosure provides a mounting assembly for attaching a magnetic field generator to a patient table. The mounting assembly allows for the secure attachment of the magnetic field generator to the patient table while also allowing for easy adjustment of the positioning and location of the magnetic field generator, even after the patient is on the table. In many embodiments the mounting assembly is comprised of a mounting apparatus that attaches directly to the patient table and first and second side rails that attach to the magnetic field generator and are configured to slidably attach to the mounting apparatus. In some embodiments, the mounting apparatus and side rails are constructed of a material that provides little or no interference with the magnetic field generator.

20 Claims, 6 Drawing Sheets

(51) Int. Cl.
*A61B 5/05* (2006.01)
*A61B 5/00* (2006.01)
*A61M 25/01* (2006.01)
*A61G 13/12* (2006.01)
*A61B 34/20* (2016.01)
*A61B 34/00* (2016.01)

(56) References Cited

U.S. PATENT DOCUMENTS

| | | | | |
|---|---|---|---|---|
| 3,905,591 A * | 9/1975 | Schorr | ............ | A61B 6/04 5/425 |
| 4,168,793 A * | 9/1979 | Knight | ............ | A45F 3/14 224/157 |
| 4,423,914 A | 1/1984 | Vander Ley | | |
| 5,678,267 A * | 10/1997 | Kinder | ............ | A61G 7/0507 5/428 |
| 6,023,800 A * | 2/2000 | Stickley | ............ | A61G 7/0507 248/229.26 |
| 6,094,760 A * | 8/2000 | Nonaka | ............ | A61B 6/0457 5/600 |
| 6,598,275 B1 * | 7/2003 | Kolody | ............ | A61G 13/101 24/455 |
| 6,955,464 B1 * | 10/2005 | Tybinkowski | ............ | A61B 6/0457 108/143 |
| 7,520,007 B2 * | 4/2009 | Skripps | ............ | A61G 13/04 24/459 |
| 7,669,262 B2 * | 3/2010 | Skripps | ............ | A61G 13/04 5/621 |
| 7,896,177 B1 | 3/2011 | Toma | | |
| 2010/0290831 A1 | 11/2010 | Burnett et al. | | |
| 2012/0148335 A1 * | 6/2012 | Nourry | ............ | A61B 6/46 403/110 |
| 2012/0241571 A1 * | 9/2012 | Masionis | ............ | A61G 1/04 248/214 |
| 2018/0104120 A1 * | 4/2018 | Sirkin | ............ | A61G 1/04 |
| 2018/0110662 A1 * | 4/2018 | Doak | ............ | A61G 1/04 |

* cited by examiner

MOUNTING ASSEMBLY FOR A MAGNETIC FIELD GENERATOR

CROSS-REFERENCE TO RELATED APPLICATIONS

This application claims the benefit of priority to U.S. Provisional Patent Application No. 62/278,215, filed Jan. 13, 2016, entitled "MOUNTING ASSEMBLY FOR A MAGNETIC FIELD GENERATOR," the entire contents of which are hereby incorporated by reference in their entirety.

FIELD OF THE DISCLOSURE

The present disclosure relates generally to a mounting assembly for medical equipment for use in electroanatomic mapping and related procedures. In particular, the present disclosure relates to a versatile mounting assembly for easily and securely mounting a magnetic field generator underneath a patient table in a manner such that the magnetic field generator can be re-positioned easily and quickly without disturbing the patient or negatively impacting the quality of the procedure.

BACKGROUND

Electrophysiologic testing and radiofrequency ablation have evolved as curative measures for a variety of heart rhythm disturbances, which if left untreated can lead to sudden cardiac death. As experience in this field has grown, ablation is progressively being used to address more complex rhythm disturbances. Using fluoroscopy as an imaging guide, the procedure generally consists of inserting a catheter inside the heart, near the area from which originates the abnormal cardiac electrical activity, and then delivering radiofrequency currents through the catheter tip to ablate the arrhythmogenic area. Fluoroscopy is a conventional visualization technique that is useful for navigating medical devices within the body and for identifying anatomical structures and landmarks within the heart.

Electroanatomic mapping (EAM) systems may be utilized to generate three-dimensional geometric models of the heart to facilitate mapping and ablation procedures. In some cases, EAM uses a magnetic system in combination with a magnetic field generator. The magnetic field generator is typically strapped underneath the table upon which the patient is placed for the procedure. The magnetic field generator generally includes a number of coils configured to emit a low-level magnetic field that interacts with sensors located within the tip of an ablation catheter, mapping catheter, and/or any other devices tracked by the system. In many circumstances and procedures, it is desirable to move and re-position the magnetic field generator beneath the patient and table after the patient has been placed on the table.

BRIEF SUMMARY OF THE DISCLOSURE

The present disclosure provides a mounting assembly for attaching medical equipment underneath a patient table. In one particular embodiment, the present disclosure provides a mounting assembly for attaching a magnetic field generator underneath a patient table. The mounting assembly allows for the secure attachment of the magnetic field generator underneath the patient table while also allowing for easy adjustment and re-positioning of the location of the magnetic field generator, even after the patient is on the table. The re-positioning may be accomplished without the patient being moved or disturbed. In many embodiments the mounting assembly is comprised of a mounting apparatus that attaches directly underneath the patient table and first and second side rails that attach to the magnetic field generator and are configured to slidably attach to, and lock within, the mounting apparatus. In some embodiments, the mounting apparatus, side rails and all or many components thereof are constructed of a material, such as a plastic, a plastic-derived material, or carbon fiber, that provides little or no interference with the performance of the magnetic field generator. Various embodiments of the present disclosure are set forth herein.

In one embodiment, the present disclosure is directed to a mounting assembly for attaching medical equipment to a patient table. The mounting assembly comprises a mounting apparatus including: (i) at least two extendable arms including means for attaching the mounting apparatus to the patient table and at least one guide rail positioned within each extendable arm; (ii) tensioning means positioned along each extendable arm for positioning and securing the mounting apparatus to the patient table; and (iii) means for coupling the at least two extendable arms. The mounting assembly also includes first and second side rails configured to be slidably attached to the mounting apparatus and configured to be attached to the medical equipment.

In another embodiment, the present disclosure is directed to a mounting assembly for attaching a magnetic field generator to a patient table. The mounting assembly comprises a mounting apparatus including: (i) a first and a second extendable arm including a beveled hook at each end thereof for attaching the mounting apparatus to the patient table; (ii) a guide rail positioned within each of the first and second extendable arm; (iii) tensioning bands positioned along each of the first and second extendable arm for positioning and securing the mounting apparatus to the patient table; and (iv) a coupling rod positioned between the first and second extendable arms at each end thereof. The mounting assembly additionally includes first and second side rails configured to be slidably attached to the first and second extendable arms, respectively, and configured to be attached to the magnetic field generator.

In another embodiment, the present disclosure is directed to a method for securing a medical device to a patient table. The method comprises (1) providing a mounting apparatus comprising: (i) a first and a second extendable arm each including a beveled hook at each end thereof and a t-shaped tongue along a length thereof (ii) a guide rail positioned within each of the first and second extendable arm; (iii) tensioning bands positioned along each of the first and second extendable arm; and (iv) a coupling rod positioned between the first and second extendable arms at each end thereof; (2) attaching a first and second side rail to a respective side of the medical device, each of the first and second side rails including a t-shaped groove configured to cooperate with the t-shaped tongue; (3) coupling the mounting apparatus to the patient table by: (i) affixing a first end of the mounting apparatus to the patient table by positioning each beveled hook on the first end of the mounting apparatus about a first edge of the patient table; (ii) opening the mounting apparatus by pulling on a second end of the mounting apparatus; (iii) positioning each beveled hook on the second end of the mounting apparatus about a second edge of the patient table; and (iv) releasing the second end of the mounting apparatus such that the tensioning bands secure the mounting apparatus to the patient table; and (4) sliding the medical device onto mounting apparatus via the t-shaped tongue and groove.

The foregoing and other aspects, features, details, utilities and advantages of the present disclosure will be apparent from reading the following description and claims, and from reviewing the accompanying drawings.

BRIEF DESCRIPTION OF THE DRAWINGS

Corresponding reference characters indicate corresponding parts throughout the several views of the drawings. It is understood that that Figures are not necessarily to scale.

DETAILED DESCRIPTION OF THE DISCLOSURE

Figure 1:
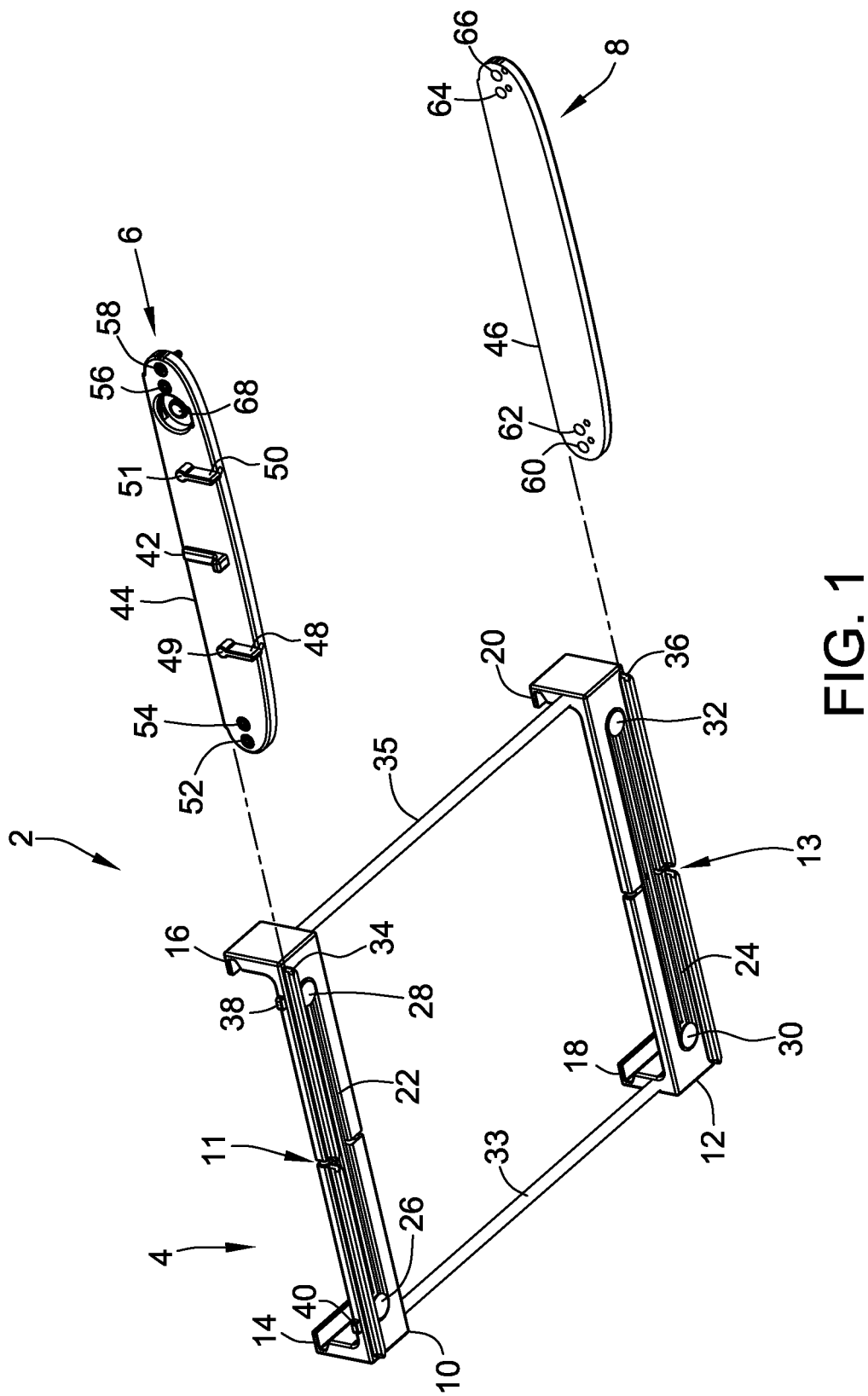
FIG. 1 illustrates a mounting assembly in accordance with one embodiment of the present disclosure.

The present disclosure provides mounting assemblies for medical equipment to be mounted to a patient table. In many embodiments, the mounting assemblies are customized to allow for the mounting of a magnetic field generator underneath a patient table. Mounting assemblies of the multiple embodiments of the present disclosure provide a number of benefits and improvements over conventional mounting systems for medical equipment such as magnetic field generators including, for example, the ability to securely and quickly attach the magnetic field generator to a wide variety of patient table designs, including tables having various widths and lengths. This attachment may be accomplished in accordance with the present disclosure by a single person, without the use of tools traditionally required for mounting medical equipment. Additionally, the mounting assemblies described herein provide the ability to re-position the magnetic field generator relative to a patient after the patient has been placed onto the table; this results in quicker, more efficient, re-positioning with little to no disturbance to the patient. Moreover, because the mounting assemblies described herein may be substantially or wholly constructed of non-magnetic and x-ray translucent materials, the mounting assemblies will not substantially affect the magnetic field produced by the magnetic field generator nor will it substantially interfere with any images produced by fluoroscopy during a procedure.

More specifically, the embodiments of the present disclosure provide a mounting assembly for attaching a magnetic field generator to the underside of a patient table wherein the mounting assembly includes a mounting apparatus and at least two side rails. The mounting apparatus includes at least two extendible arms that include a means for attaching the mounting apparatus to the patient table and allow for its use on various sized patient tables. Positioned within the extendable arms are tensioning members or devices for sizing and securing the mounting apparatus to a patient table. The extendable arms are coupled together using a coupling means such as rods in many embodiments. The mounting assembly additionally includes first and second side rails that are configured to be slidably attached to the mounting apparatus and also configured to be attached to the magnetic field generator. The side rails may be attached to the magnetic field generator using screws, bolts, or other means, for example. The mounting assemblies additionally provide one or more locking and safety mechanisms.

For purposes of this description, the mounting assemblies of the present disclosure will be primarily described in connection with the mounting of a magnetic field generator underneath a patient table. It is contemplated, however, that the described features and methods of the mounting assemblies and the components thereof of present disclosure as described herein may be used in combination with the mounting of other medical equipment to a patient table or other equipment as would be appreciated by one of ordinary skill in the art based on the disclosure herein.

Referring now to the drawings, and specifically to FIG. 1, there is shown a mounting assembly 2 that includes mounting apparatus 4 (in a closed or non-extended position) and first side rail 6 and second side rail 8. Mounting apparatus 4 includes a first extendable arm 10 and a second extendable arm 12. First extendable arm 10 is configured to be separated (extended or expanded, see FIG. 3 below) at junction 11 and second extendable arm 12 is configured to be separated (extended or expanded, see FIG. 3 below) at junction 13. First extendable arm 10 includes beveled hooks 14 and 16 and second extendable arm includes beveled hooks 18 and 20. Beveled hooks 14, 16, 18, and 20 allow mounting apparatus 4 to be attached to a patient table or other equipment (not shown in FIG. 1), and are further discussed below in reference to FIG. 4. Although shown as beveled hooks 14, 16, 18, and 20 in FIG. 1, any suitable means for attaching mounting apparatus 4 to a patient table may be included on first extendable arm 10 and second extendable arm 12 to allow attachment to a patient table. The other suitable attachment means may be beveled or non-beveled.

Referring again to FIG. 1, mounting apparatus 4 additionally includes a tensioning means 22 and 24 positioned along first extendable arm 10 and second extendable arm 12, respectively. Tensioning means 22 and 24 allow first extendable arm 10 and second extendable arm 12 to be extended or expanded to open the mounting apparatus such that upon attaching to a patient table (not shown in FIG. 1, but see FIGS. 5 and 6), tensioning means 22 and 24 retract to secure mounting apparatus 4 to the patient table; that is, tensioning means 22 and 24 allow for mounting apparatus 4 to be customized to fit patient tables of various widths. Tensioning means 22 and 24 may be any suitable tensioning means such as, for example tensioning bands (expandable bands), springs, and the like, and combinations thereof. Tensioning bands constructed of neoprene or a similar material are desirable in some embodiments. Tensioning means 22 is attached to first extendable arm 10 by coupling pins 26 and 28 and tensioning means 24 is attached to second extendable arm 12 by coupling pins 30 and 32. The coupling pins may be attached to the extendable arms by any suitable means including for example, by pressure fit methods. Mounting apparatus 4 additionally includes coupling rods 33 and 35 to couple first extendable arm 10 and second extendable arm 12 together. Any suitable means may be used to couple first extendable arm and second extendable arm together, as would be recognized by one skilled in the art based on the disclosure herein.

Mounting apparatus 4 additionally includes t-shaped tongue 34 and safety catch stops 38 and 40 on first extendable arm 10 and t-shaped tongue 36 on second extendable arm 12 as again illustrated in FIG. 1. T-shaped tongues 34 and 36 allow groove 44 of first side rail 6 and groove 46 of second side rail 8 to slide onto and cooperate with a corresponding tongue located on first extendable arm 10 and second extendable arm 12 respectively, as described herein. Safety catch stops 38 and 40 are configured to interact with safety catch 42 on first side rail 6 such that medical equipment, such as a magnetic field generator (not shown in FIG. 1 but see FIGS. 5 and 6) cannot inadvertently slide off of mounting apparatus 4. First side rail 6 additionally includes lateral position lock down levers 48 and 50 having beveled surfaces 49 and 51 that are configured to interact with respective push pins (not shown in FIG. 1 but see FIG. 2) within first side rail 6 to secure first side rail 6 to first extendable arm 10. First side rail 6 includes openings 52, 54, 56, and 58 and second side rail 8 both includes openings 60, 62, 64, and 66 to allow first side rail 6 and second side rail 8 to be connected or attached (through a desirable means such as a bolt or screw) to a piece of medical equipment, such as a magnetic field generator (not shown in FIG. 1). First side rail 6 also includes aperture 68 to allow an electrical connector (or other cords or equipment, not shown in FIG. 1) to pass through first side rail 6 and a mating connector located on the medical equipment (not shown in FIG. 1). Mounting apparatus 4, first side rail 6, second side rail 8, and all components thereof may be constructed of carbon fibers, thermoplastics, acrylonitrile butadiene styrene, and combinations thereof so as to reduce or eliminate any interference with the procedure being performed.

Figure 2:
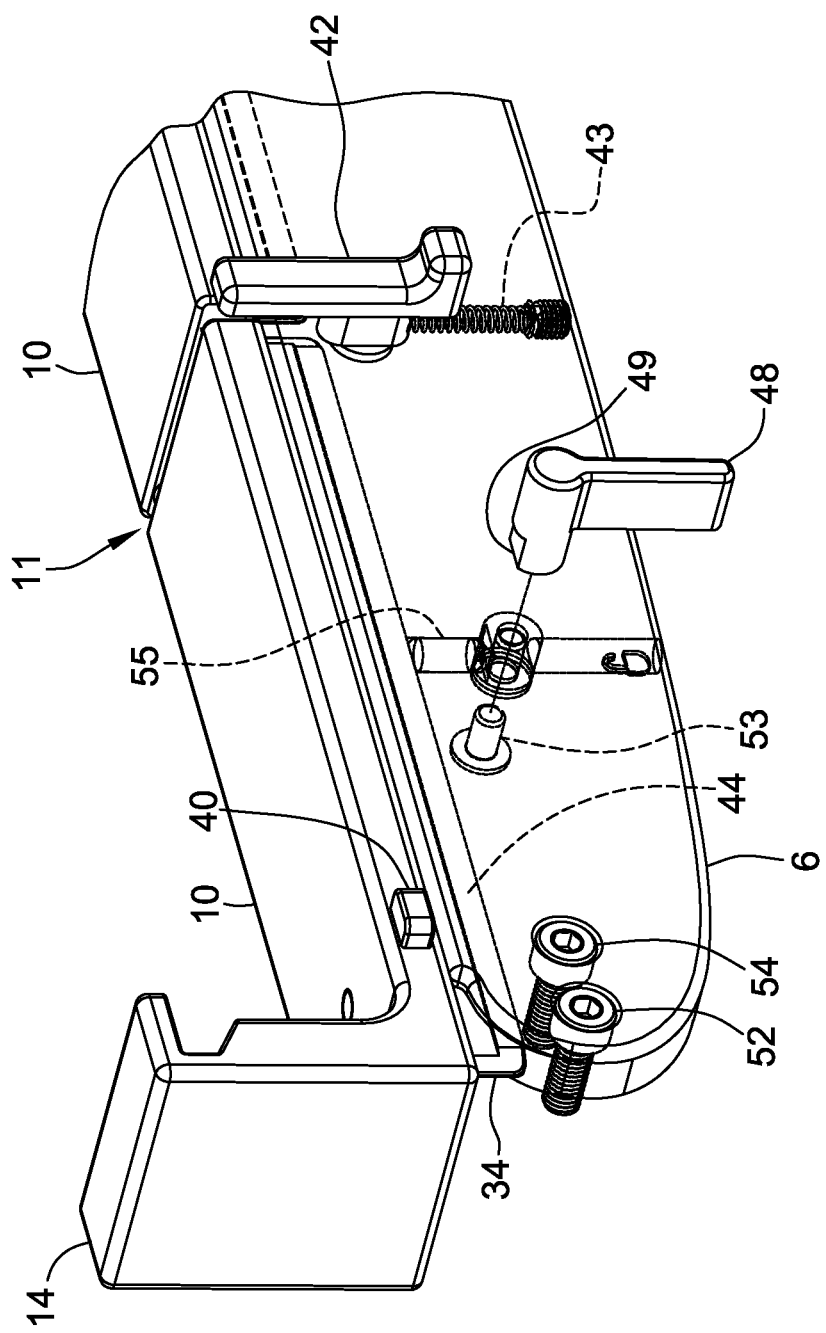
FIG. 2 illustrates a mounting apparatus in sliding communication with a first side rail in accordance with one embodiment of the present disclosure.

Referring now to FIG. 2, there is illustrated a portion of a mounting apparatus in slidable communication with a single side rail as illustrative of how the mounting apparatus and side rails come together to form the mounting assembly. FIG. 2 shows first extension arm 10 having junction 11, beveled hook 14 and safety catch stop 40 in slidable communication with first side rail 6. As illustrated, t-shaped tongue 34 on first extension arm 10 is slidably engaged with groove 44 of first side rail 6. First side rail 6 is shown with safety catch 42, connected to spring action 43, which provides safety catch 42 with a spring-loaded mechanism, lateral position lock down lever 48 including beveled surface 49 and lock pin 53, as well as openings 52 and 54.

Figure 3:
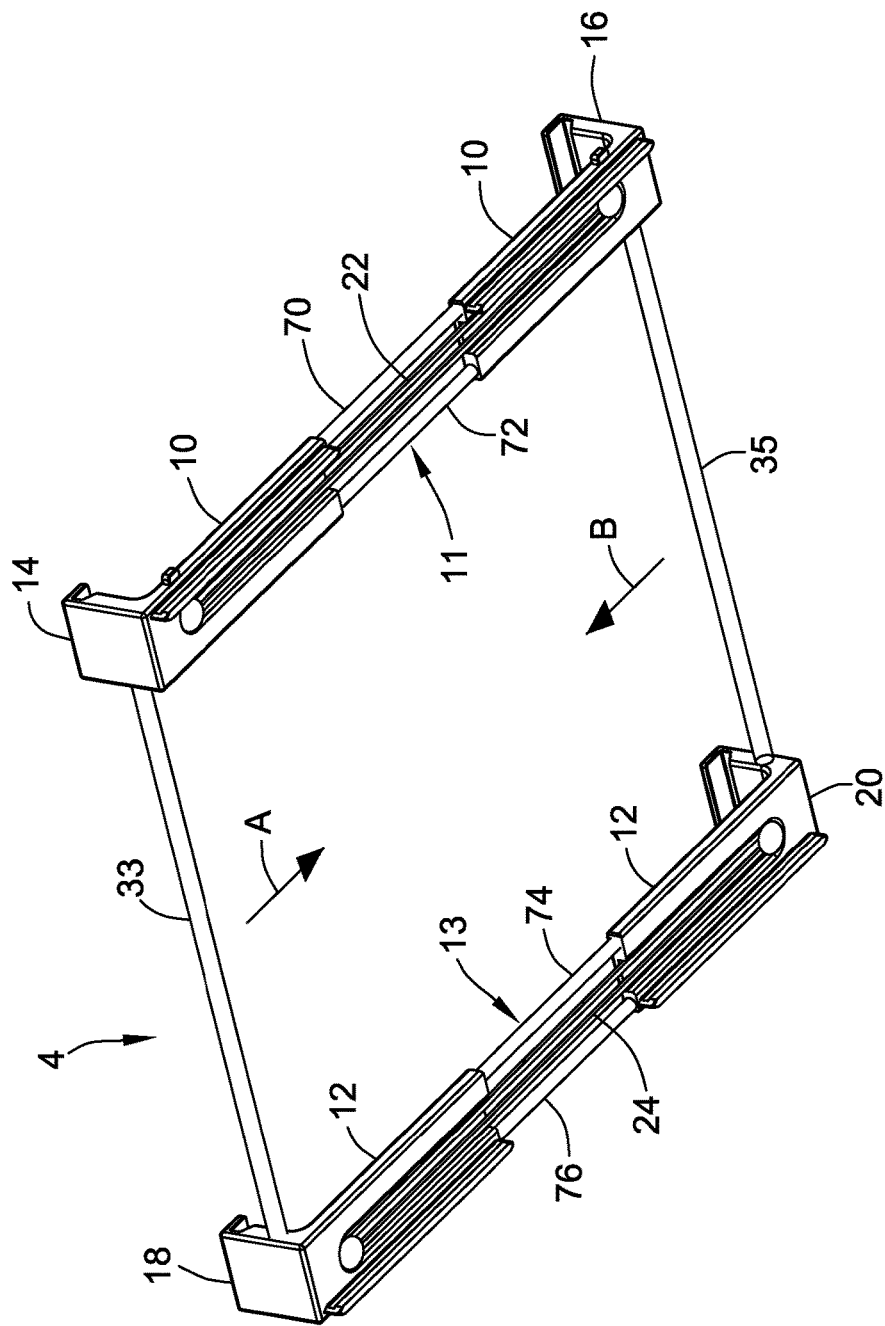
FIG. 3 illustrates a mounting apparatus in an extended or expanded configuration in accordance with one embodiment of the present disclosure.

Referring now to FIG. 3, there is illustrated mounting apparatus 4 in an extended or expanded configuration such that there is increased tension on tensioning means 22 and 24 (as compared to a non-expanded or non-extended position) pulling beveled hooks 14 and 18 along line A and beveled hooks 16 and 20 along line B. First extendable arm 10 is separated at junction 11 and second extendable arm 12 is separated at junction 13. In this configuration, guide rails 70 and 72 in first expandable arm 10 and guide rails 74 and 76 in second expandable arm 12 are shown. These guide rails 70, 72, 74, and 76 act to prevent misalignment and/or deformation of the extendable arms upon expanding and contracting thereof, while providing strength to mounting apparatus 4. As noted above, this extended or expanded configuration of mounting apparatus 4 allows for mounting apparatus 4 to be easily positioned on a patient's table.

Figure 4:
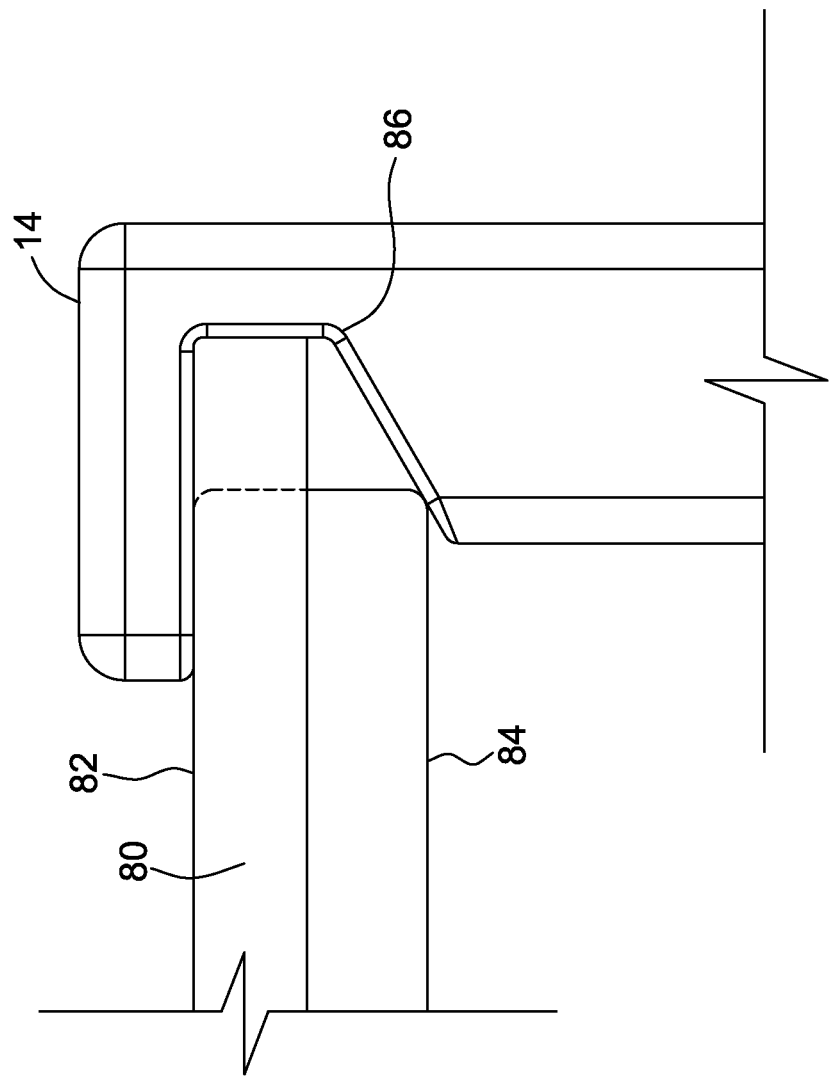
FIG. 4 illustrates one embodiment of an attachment means for a mounting apparatus in accordance with one embodiment of the present disclosure.

As noted above, the mounting assembly described herein in one embodiment provides a means for the mounting apparatus portion of the mounting assembly to be attached to a table, and desirably a table for holding a patient during a medical or other procedure. In some embodiments, the attachment means are designed to provide attachment to a multitude of patient tables and designs, including tables of various thicknesses. FIG. 4 illustrates one embodiment of a beveled hook attachment means of the present disclosure as described herein. FIG. 4 shows beveled hook 78 attached to table 80. Beveled hook 78 contacts both upper surface 82 of table 80 and lower surface 84 of table 80 to provide a secure attachment. Because of beveled edge 86 on beveled hook 78, beveled hook 78 can accommodate tables having variable widths; that is, beveled hook 78 allows this attachment means to be suitable for use with a wide range of tables of various thicknesses using a single attachment means. In some embodiments the surface of beveled edge 86 may be coated by a friction-increasing material or compound to increase the gripping ability of beveled edge 86.

As noted and described herein, the first and second side rails of the mounting assembly of the present disclosure are sized and configured to have a piece of medical equipment, such as a magnetic field generator, attached thereto. Once the medical equipment is attached to the first and second side rails, the side rails are slid into the mounting apparatus as described above. The first and second side rails including the medical apparatus may be slid into the mounting apparatus prior to the mounting apparatus being attached to a patient table, or the mounting apparatus may first be attached to the patient table and then the side rails including the medical equipment may be slid into the mounting apparatus. In many embodiments, it is desirable to first attach the mounting apparatus to the patient table and then slide the first and second side rails into the mounting apparatus to suitably position the piece of medical equipment under the patient table.

Figure 5:
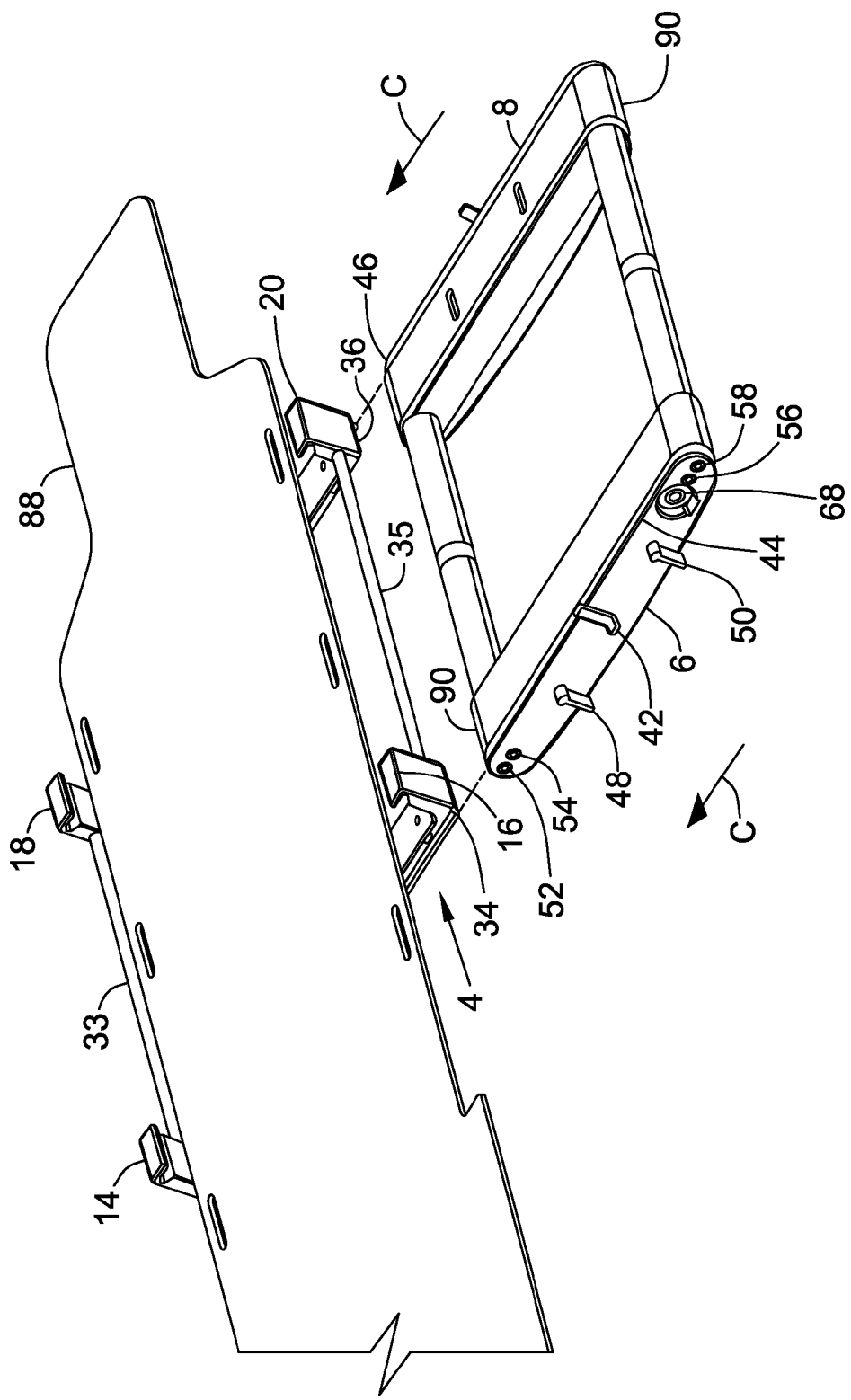
FIG. 5 illustrates one suitable embodiment for utilizing the mounting apparatus and side rails described herein in accordance with the present disclosure to position a piece of medical equipment beneath a patient table.

Referring now to FIG. 5, there is illustrated a suitable setup for utilizing the mounting apparatus and side rails described herein in accordance with the present disclosure to position a piece of medical equipment beneath a patient table. FIG. 5 shows a patient table 88 and mounting apparatus 4 for attaching to patient table 88 via beveled hooks 14, 16, 18, and 20. First side rail 6 and second side rail 8 are coupled to magnetic field generator 90 via screws (not shown in FIG. 5) in openings 52, 54, 56, and 58 in first side rail 6 and via openings 60, 62, 64, and 66 (not shown in FIG. 5 but see FIG. 1) in second side rail 8. First side rail 6 and second side rail 8 may be slidably attached to mounting apparatus 4 via the introduction of t-shaped tongues 34 and 36 on first side rail 6 and second side rail 8 into grooves 44 and 46, respectively, by moving first and second side rails 6 and 8 along line C to position magnetic field generator 90 underneath patient table 88. First and second side rails 6 and 8 including magnetic field generator 90 may then be locked onto mounting apparatus 4 via lateral position lock down lever 48 and 50, as described herein.

Figure 6:
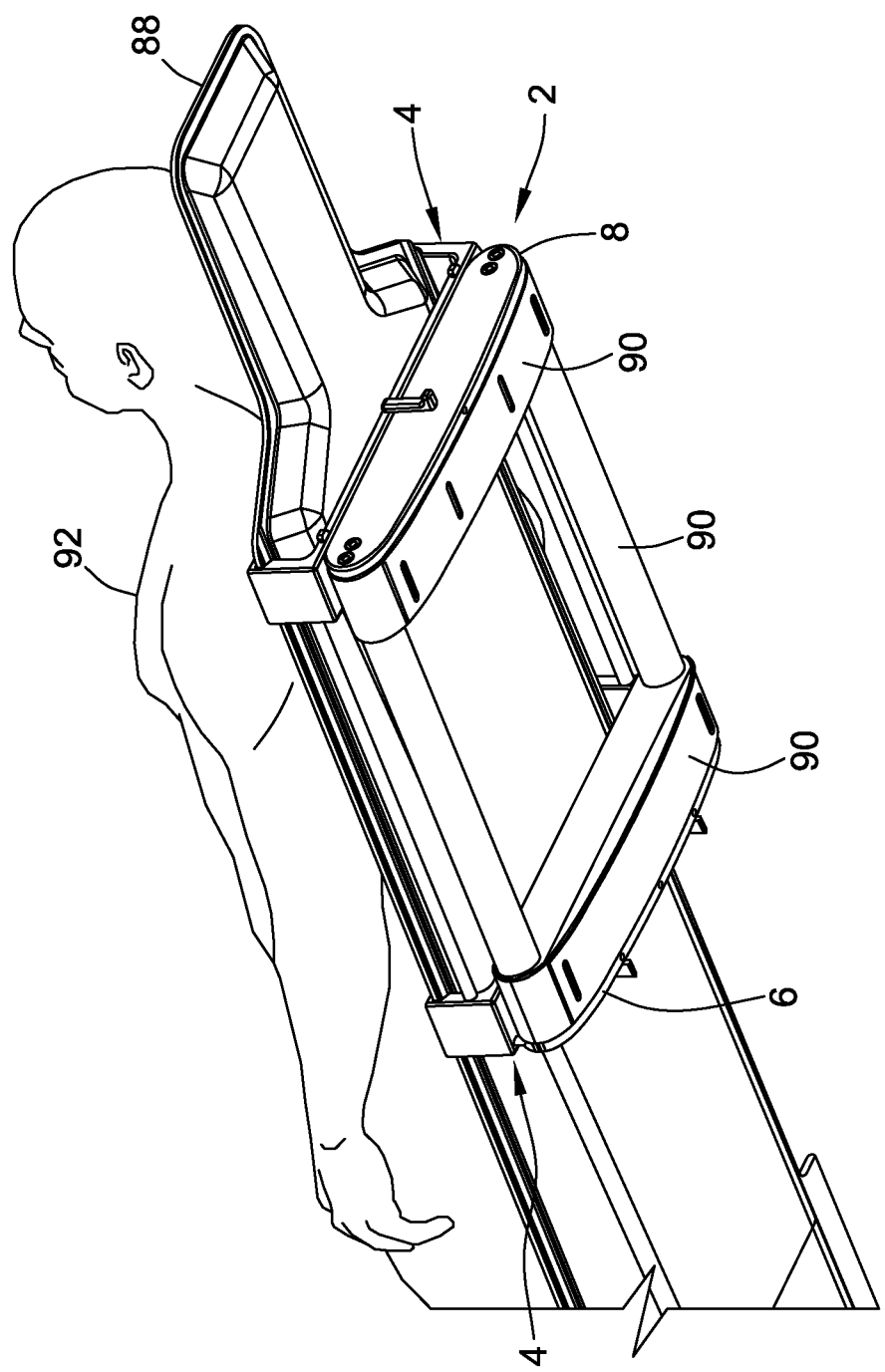
FIG. 6 illustrates a mounting assembly of the present disclosure in combination with a magnetic field generator securely mounted underneath a patient table.

Referring now to FIG. 6, there is shown the mounting assembly of the present disclosure, including a magnetic field generator, mounted underneath a patient table. Specifically, FIG. 6 illustrates mounting assembly 2 including mounting apparatus 4 and first side rail 6 and second side rail 8, with magnetic field generator 90 coupled thereto, mounted to patient table 88 underneath patient 92. In accordance with the present disclosure, mounting assembly 2 can be easily de-coupled from patient table 88 and re-positioned as desired before, during, or after a procedure with magnetic field generator 90 in place.

The present disclosure also relates to methods of using the mounting assemblies described herein to secure medical equipment, such as a magnetic field generator, to a table, including a patient's table, such that the medical equipment may be easily de-coupled from the table and re-positioned as desired. The re-positioning of the medical equipment, using the extendable arms of the mounting apparatus as described above, may be done easily and efficiently even while the patient is on the table; that is, there is no need to move the patient to reposition the medical equipment before, during, or after a procedure.

In one specific embodiment of the present disclosure, a method for securing a medical device to a patient table is disclosed. The method comprises: (i) providing a mounting apparatus, the mounting apparatus comprising: (a) a first and a second extendable arm each including a beveled hook at each end thereof and a t-shaped tongue along a length thereof; (b) a guide rail positioned within each of the first and second extendable arm; (c) tensioning bands positioned along each of the first and second extendable arm; and (d) a coupling rod positioned between the first and second extendable arms at each end thereof; (ii) attaching first and second side rails to a respective side of the medical device, each of the first and second side rails including a t-shaped groove configured to cooperate with the t-shaped tongue; (iii) coupling the mounting apparatus to the patient table by: (a) affixing a first end of the mounting apparatus to the patient table by positioning each beveled hook on the first end of the mounting apparatus about a first edge of the patient table; (b) opening the mounting apparatus by pulling on a second end of the mounting apparatus; (c) positioning each beveled hook on the second end of the mounting apparatus about a second edge of the patient table; and (d) releasing the second end of the mounting apparatus such that the tensioning bands secure the mounting apparatus to the patient table; and (iv) sliding the medical device onto mounting apparatus via the t-shaped tongue and groove. Once the medical device is slid into position within the mounting apparatus, it may be secured in place within the mounting apparatus using the lateral position lock down levers described herein.

Although certain embodiments of this disclosure have been described above with a certain degree of particularity, those skilled in the art could make numerous alterations to the disclosed embodiments without departing from the spirit or scope of this disclosure. All directional references (e.g., upper, lower, upward, downward, left, right, leftward, rightward, top, bottom, above, below, vertical, horizontal, clockwise, and counterclockwise) are only used for identification purposes to aid the reader's understanding of the present disclosure, and do not create limitations, particularly as to the position, orientation, or use of the disclosure. Joinder references (e.g., attached, coupled, connected, and the like) are to be construed broadly and may include intermediate members between a connection of elements and relative movement between elements. As such, joinder references do not necessarily infer that two elements are directly connected and in fixed relation to each other. It is intended that all matter contained in the above description or shown in the accompanying drawings shall be interpreted as illustrative only and not limiting. Changes in detail or structure may be made without departing from the spirit of the disclosure as defined in the appended claims.

When introducing elements of the present disclosure or the preferred embodiment(s) thereof, the articles "a", "an", "the", and "said" are intended to mean that there are one or more of the elements. The terms "comprising", "including", and "having" are intended to be inclusive and mean that there may be additional elements other than the listed elements.

As various changes could be made in the above constructions without departing from the scope of the disclosure, it is intended that all matter contained in the above description or shown in the accompanying drawings shall be interpreted as illustrative and not in a limiting sense.

What is claimed is:

1. A mounting assembly for attaching medical equipment to a patient table, the mounting assembly comprising:
   a mounting apparatus including:
      at least two extendable arms including means for attaching the mounting apparatus to the patient table and at least one guide rail positioned within each extendable arm;
      tensioning means positioned along each extendable arm for positioning and securing the mounting apparatus to the patient table; and
      means for coupling the at least two extendable arms; and
   first and second side rails configured to be slidably attached to the mounting apparatus and configured to be attached to the medical equipment.

2. The mounting assembly of claim 1, wherein the means for attaching the mounting apparatus to the patient table includes a beveled hook positioned at each end of the at least two extendable arms.

3. The mounting assembly of claim 1, wherein each extendable arm comprises a single arm configured to be separated along the tensioning means.

4. The mounting assembly of claim 1, wherein each extendable arm includes a t-shaped tongue configured to cooperate with a respective first and second side rail.

5. The mounting assembly of claim 1, wherein each extendable arm is constructed of a material selected from the group consisting of carbon fibers, thermoplastics, acrylonitrile butadiene styrene, and combinations thereof.

6. The mounting assembly of claim 1, wherein the tensioning means is selected from the group consisting of expandable bands, springs, or combinations thereof.

7. The mounting assembly of claim 6, wherein the tensioning means comprises at least one neoprene band.

8. The mounting assembly of claim 1, wherein the tensioning means are coupled to the first and second extendable arms via a coupling pin pressure-fit into the extendable arm.

9. The mounting assembly of claim 1, wherein the means for coupling the at least two extendable arms comprises carbon fiber rods.

10. The mounting assembly of claim 1, wherein the least one extendable arm includes a safety catch stop.

11. The mounting assembly of claim 10, wherein at least one of the first and second side rails includes a safety catch configured to cooperate with the safety catch stop.

12. The mounting assembly of claim 1, wherein the first and second side rails each include a groove configured to cooperate with a respective expandable arm.

13. The mounting assembly of claim 1, wherein at least one of the first and second rails includes a lateral position lock-down lever for securing the respective side rail to an expandable arm.

14. The mounting assembly of claim 13, wherein the lateral position lock-down lever includes a beveled surface for communication with a lock-down pin.

15. The mounting assembly of claim 1, wherein each of the first and second side rails includes a means for attaching each of the first and second side rails to the medical equipment.

16. The mounting assembly of claim 1, wherein the medical equipment is a magnetic field generator.

17. A mounting assembly for attaching a magnetic field generator to a patient table, the mounting assembly comprising:

a mounting apparatus including:
  a first and a second extendable arm including a beveled hook at each end thereof for attaching the mounting apparatus to the patient table;
  a guide rail positioned within each of the first and second extendable arm;
  tensioning bands positioned along each of the first and second extendable arm for positioning and securing the mounting apparatus to the patient table; and
  a coupling rod positioned between the first and second extendable arms at each end thereof; and
  first and second side rails configured to be slidably attached to the first and second extendable arms, respectively, and configured to be attached to the magnetic field generator.

18. The mounting assembly of claim 17, wherein the first and second side rails each include a safety catch configured to cooperate with a safety catch stop positioned on a respective expandable arm.

19. The mounting assembly of claim 17, wherein at least one of the first and second side rails includes a lateral position lock-down lever for securing the side rail to a respective expandable arm.

20. A method for securing a medical device to a patient table, the method comprising:
  providing a mounting apparatus, the mounting apparatus comprising:
    a first and a second extendable arm each including a beveled hook at each end thereof and a t-shaped tongue along a length thereof;
    a guide rail positioned within each of the first and second extendable arm;
    tensioning bands positioned along each of the first and second extendable arm; and
    a coupling rod positioned between the first and second extendable arms at each end thereof;
  attaching first and second side rails to a respective side of the medical device, each of the first and second side rails including a t-shaped groove configured to cooperate with the t-shaped tongue;
  coupling the mounting apparatus to the patient table by:
    affixing a first end of the mounting apparatus to the patient table by positioning each beveled hook on the first end of the mounting apparatus about a first edge of the patient table;
    opening the mounting apparatus by pulling on a second end of the mounting apparatus;
    positioning each beveled hook on the second end of the mounting apparatus about a second edge of the patient table; and
    releasing the second end of the mounting apparatus such that the tensioning bands secure the mounting apparatus to the patient table; and
  sliding the medical device onto mounting apparatus via the t-shaped tongue and groove.

* * * * *